United States Patent
Koseki

(10) Patent No.: US 6,918,915 B2
(45) Date of Patent: Jul. 19, 2005

(54) MAXILLARY BONE EXTENSOR

(75) Inventor: Tomoaki Koseki, Chiyoda-ku (JP)

(73) Assignee: Koseki Medical K.K., Tokyo (JP)

( * ) Notice: Subject to any disclaimer, the term of this patent is extended or adjusted under 35 U.S.C. 154(b) by 105 days.

(21) Appl. No.: 10/275,835

(22) PCT Filed: Mar. 11, 2002

(86) PCT No.: PCT/JP02/02235

§ 371 (c)(1),
(2), (4) Date: Nov. 9, 2002

(87) PCT Pub. No.: WO02/076313

PCT Pub. Date: Oct. 3, 2002

(65) Prior Publication Data

US 2003/0139748 A1 Jul. 24, 2003

(30) Foreign Application Priority Data

Mar. 12, 2001 (JP) .......................................... 2001-69269

(51) Int. Cl.[7] .............................................. A61B 17/58
(52) U.S. Cl. ........................... 606/90; 606/53; 606/105; 433/7
(58) Field of Search ........................... 606/90, 53, 105, 606/57, 58, 60, 70, 71, 69; 433/7

(56) References Cited

U.S. PATENT DOCUMENTS

| 4,096,857 | A |   | 6/1978 | Cramer et al. |
| 5,364,396 | A |   | 11/1994 | Robinson |
| 5,807,382 | A | * | 9/1998 | Chin ............................ 606/53 |
| 5,885,283 | A | * | 3/1999 | Gittleman .................... 606/57 |
| 6,007,535 | A | * | 12/1999 | Rayhack et al. .............. 606/57 |
| 6,277,124 | B1 | * | 8/2001 | Haag ........................... 606/105 |
| 6,423,069 | B1 | * | 7/2002 | Sellers ......................... 606/71 |

FOREIGN PATENT DOCUMENTS

| JP | 61-47098 | 10/1986 |
| JP | 9-215699 | 8/1997 |
| JP | 10-43203 | 2/1998 |
| JP | 11-262491 | 9/1999 |
| JP | 2000-316891 | 11/2000 |
| WO | WO 97/14367 | 4/1997 |

* cited by examiner

Primary Examiner—Pedro Philogene

(57) ABSTRACT

A maxilla extension apparatus that extends the maxilla in lower forward direction, wherein a band is installed on the maxilla dentition, fixed onto a slide rail, and an arm is fixed onto the zygomatic bone. With this embodiment, a maxilla extension apparatus can be offered, an apparatus of which can accurately and less invasively extend the maxilla in a short time.

2 Claims, 2 Drawing Sheets

MAXILLARY BONE EXTENSOR

BACKGROUND OF THE INVENTION

1. Field of the Invention

This invention relates to an apparatus utilized to conduct maxilla extension surgery in cases of maxilla regressive growth and mandible excessive growth.

2. Description of the Prior Art

Disorders such as maxilla regressive growth and mandible excessive growth represented by harelip and cleft palate symptoms, occur with abnormal occlusion in which the upper and lower jaw bones do not bite, and cause declined tongue disposition and muscle function abnormalities. A conventional treatment conducted on maxilla regressive growth patients is to fix elastic rubber on the canine tooth of the maxilla dentition part, give some pulling force forward to open the maxilla peripheral sutura, and promote bone repair. Another conventional method is to incise the maxilla, and move the maxilla forward surgically.

SUMMARY OF THIS INVENTION

The treatment period for fixing elastic rubber on the maxilla dentition canine tooth and pulling the jaw forward would take about 1 to 2 years, but this method can extend the bone for only 1 to 2 mm, a treatment of which is not adaptable for patients with notable harelip or cleft palate cases. Also, as the treatment takes a long time, it is difficult to maintain cooperation from the patients for such an extended period of time. The surgical method to incise the maxilla and move the maxilla forward, is highly invasive, and would generate issues such as necrosis of the dental pulp in connection with the bone incision, and disorder of nasopharynx occlusive functions The nasal maxilla complex has the skeletal structure with many suturae, and the sutura parts open during the growth period, to let grow and extend the bone tissue. Therefore, it is possible to promote and accelerate the bone growth by placing some mechanical burden on this part.

This invention enables the acceleration of bone growth in a short time such as one week, by directly fixing the zygomatic bone and the maxilla dentition, placing mechanical burden by supplying rotation force with a rotation shaft from the inside of the mouth. As the shaft can be removed and is detachable, the fact that a maxilla extension apparatus is mounted inside is not so obvious from the outside. Once the bone is extended, the maxilla extension apparatus is removed after a certain fixation period, and the removal can be done easily by unfastening the screw on the zygomatic bone side, and by unfastening the band on the maxilla dentition, a method of which is highly non-invasive compared to conventional bone incision method.

DESCRIPTION OF THE PREFERRED EMBODIMENTS

Hereafter, a description of the preferred embodiments of this invention is made in reference to drawings. FIG. 1 is a drawing of an embodiment of this invention. FIG. 1 shows a maxilla extension apparatus installed onto the left part of a face. The maxilla is approached from the inside of the mouth, after which the oral membrane is incised, the position of the Zygomatic bone maxilla sutura 14 is confirmed, then the tip of Zygomatic bone fixing arm 2 is fixed onto Zygomatic bone 10 at the end of the seam. FIG. 1 shows that a Flexible metal 13 is spread like a maple leaf, and the tip ends of the metal are fixed onto the root part with Screw 12. The material of the flexible metal should be pure titanium or stainless steel SUS316L and such, materials with high compatibility with body parts. Zygomatic bone fixing arm 2 is connected with Flexible metal 12 with welding, to assure sufficient hardness. The Forward extension shaft 7 and Angle adjustment rotation shaft 6 both of which are extruded, are used to adjust the extension length and the angle with Driver 8. The target growth for the bone extension is 1 mm per day, for reference. Usually, 3 to 4 mm of growth is sufficient in many cases, but there are cases in which the growth should be approximately 1 cm. The length of the growth extension can be controlled easily with the screw pitch set at 1 mm per rotation. Idealistically, the bone growth can effectively be accelerated when the apparatus is tilted at an angle of 38 degrees to the lower side, measured from the bite plane. The slash marked part in the drawing shows the left nasal maxilla complex to be extended to the lower forward direction. In actual application, same apparatus is mounted on the right side, conducting extension on both sides simultaneously. FIG. 2 is a perspective drawing of the main part of this invention. Different from FIG. 1, this drawing shows the right side of a face. The head part of Angle adjustment rotation shaft 6 and Forward extension shaft 7 are formed hexagonally, which can be connected to the tip of the driver. Angle adjustment rotation shaft 6 is cylindrical when inside the main part, with screw-thread cutter in the perimeter of the cylinder, forming Screw 4. In conjunction with this screw, the inside of Angle adjustment movable cylinder 15 also has screw-thread cutter features inside. Angle adjustment shaft 3 that grasps onto the outside of the Angle movable cylinder 15 is connected, and the shaft is further connected to the center part of Zygomatic bone fixing arm 2. When Angle adjustment rotation shaft 6 is rotated, Main part 1 tilts upward or downward. Forward extension shaft 7 has the same structure, wherein the inside of the main part becomes Forward extension screw 5. Movable cylinder 16 for extension that screws onto Screw 5 is connected to Slide rail 9 via a window on Main part 1, and therefore the Slide rail 9 moves forward or backward when Forward extension shaft 7 is rotated. Metal band 11 which is made from the mold of each patient is welded onto this Slide rail 9, and the product is completed.

As in the above description, this invention enables maxilla extension in a short time, with very low invasiveness, without causing pain on the part of the patient. The surgeon can conduct treatment from the inside the mouth, obtaining good effects with simple surgery. The extension length and the angle can be managed and controlled easily, and a highly accurate adjustment is possible. Furthermore, each apparatus is used as an exclusive apparatus for each patient, and this enables the fixing force of each apparatus to be stronger, causing less uncomfortable feeling on the part of the patient.

Figure 1:
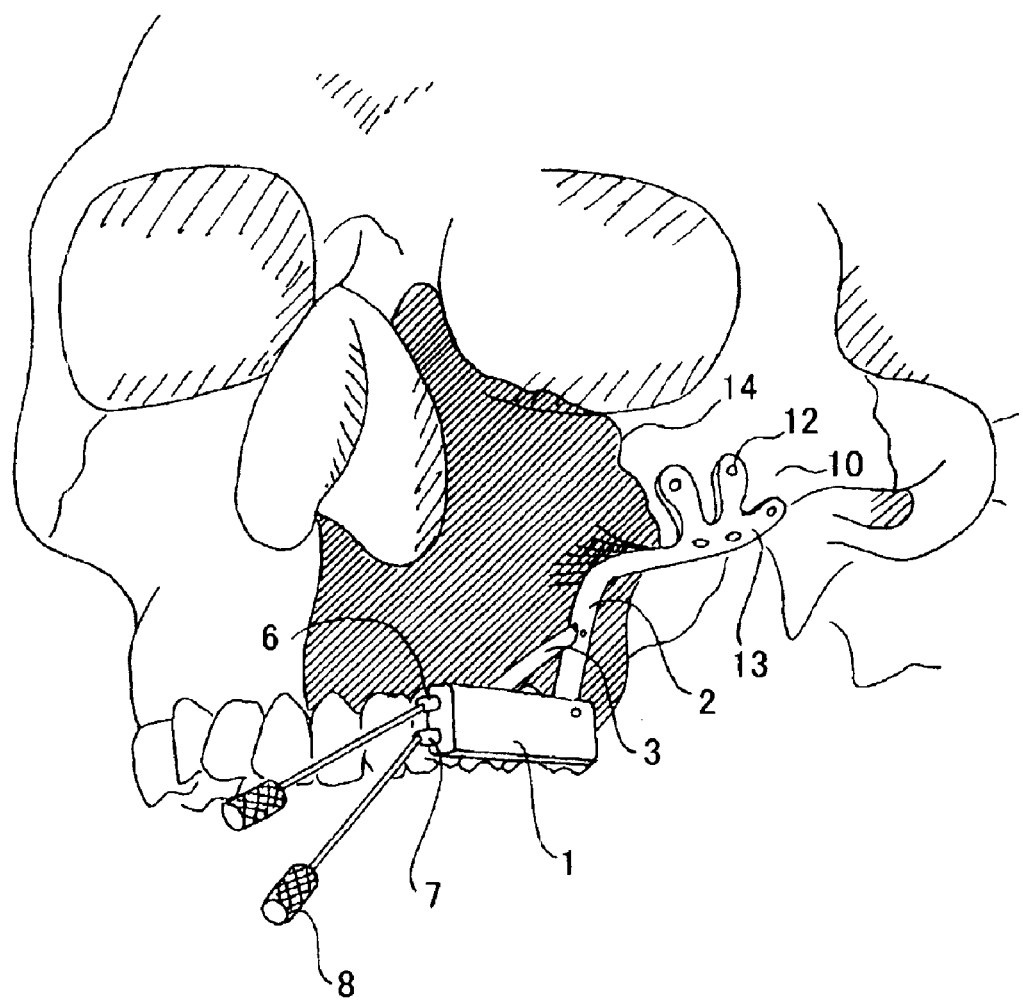
FIG. 1 is an explanatory drawing depicting an embodiment of the maxilla extension apparatus.
Figure 2:
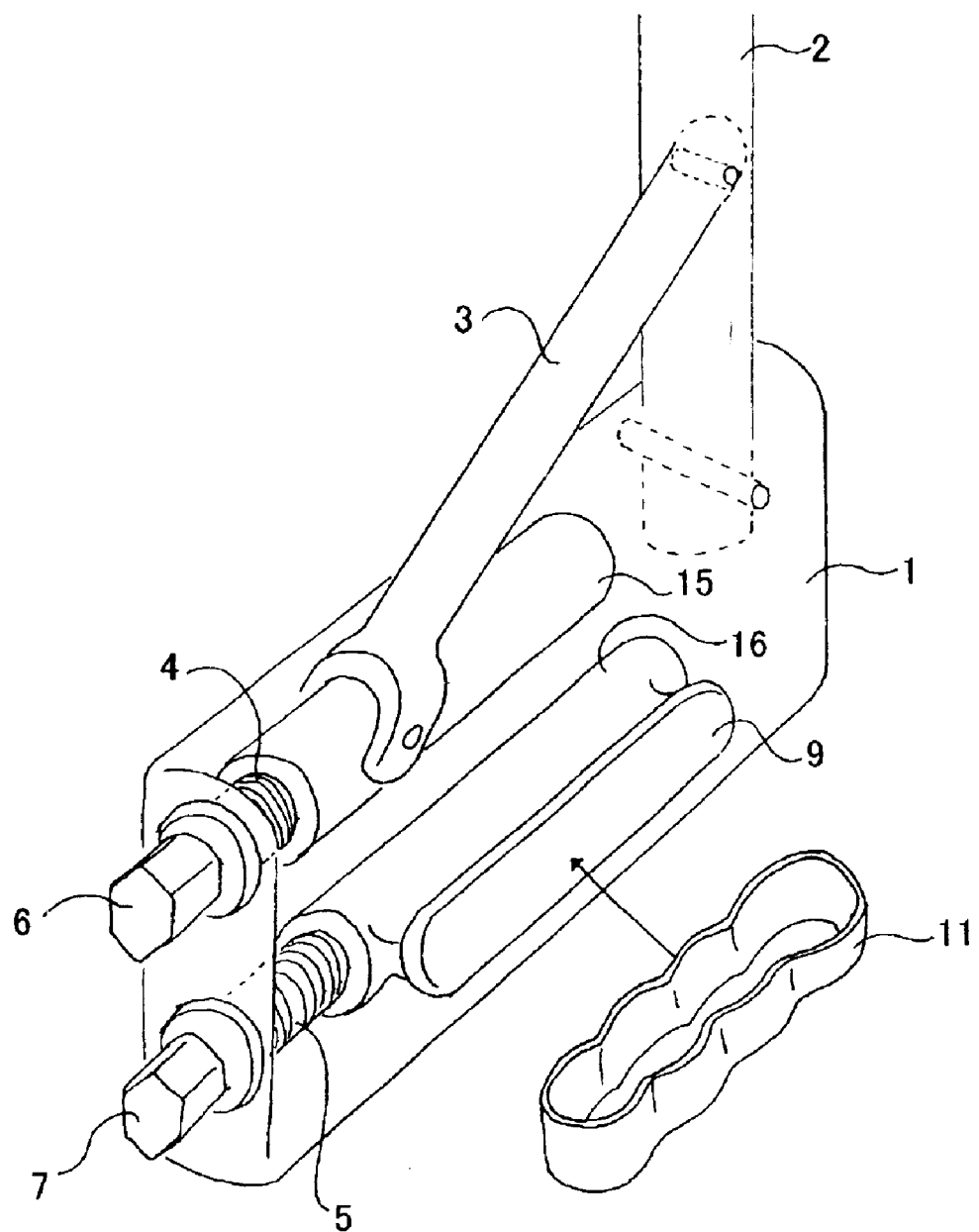
FIG. 2 is a perspective drawing of this invention.

What is claimed is:

1. A maxilla bone extension apparatus to be utilized in cases of maxilla regressive growth and mandible excessive growth, which is an apparatus to promote bone formation by pulling out a nasal maxilla complex forward and by extending maxilla peripheral sutura part, an apparatus composed of a main body, a fixing arm, a movable cylinder for forward extension, a screw for forward extension, a shaft for forward extension, an arm for angle adjustment, a movable cylinder for angle adjustment, a shaft for angle adjustment, a screw for angle adjustment, a metal sash band, and a driver, wherein, a fixing arm is connected to the rear part of the main body through a hinge, a tip end of a fixing arm is in a flexible flat form adapted to fix onto a zygomatic bone, the fixing arm tip end having a multiple number of holes to let through screws for fixing, a movable cylinder for forward extension is stored inside the main body, a side of the movable cylinder for forward extension exposed from sides of the main body, forming movable rails that can be slid forward and backward, a metal sash band to match peripheral form of a patient's right and left side molar teeth is fixed onto a movable rail exposed from the main body, thread-cutting is applied to inside of the movable cylinder for forward extension, a screw for forward extension fits inside the movable cylinder for forward extension, a tip end of the screw for forward extension is connected to a shaft for forward extension through a wall at the front side of the main body, and when the shaft for forward extension that extends to the front side of the main body is rotated with a driver, the screw for forward extension inside the main body connected to the shaft pushes forward a movable rail and connecting metal sash band, and thus maxilla bone is extended, a screw pitch inside the movable cylinder for forward extension is set so that the distance of the bone extension per one rotation of a shaft for forward extension is 1 mm which is appropriate for the amount of bone growth per one day, a movable cylinder for angle adjustment is stored inside the main body in parallel to the movable cylinder for forward extension, a tip end of an angle adjustment arm is connected to the central part of the main body through a hinge, rear end of the angle adjustment arm is connected to the center part of the fixing arm through a hinge, inside of a movable cylinder for angle adjustment has thread-cutting applied, a screw for angle adjustment fits inside the movable cylinder for angle adjustment, a tip end of the screw for angle adjustment is connected to a shaft for angle adjustment via a wall in the front side of the main body, thus being an apparatus with a structure that when a shaft for angle adjustment is rotated with a driver a screw for angle adjustment rotates, a movable cylinder for angle adjustment moves forward and backward within the main body, the main body tilts vertically, the angle for the direction of extension can be adjusted freely, the angle adjustment function works so that a screw pitch inside the movable cylinder for angle adjustment is set to make the shaft for angle adjustment to move one degree per one rotation.

2. A manufacturing method of a maxilla bone extension apparatus according to claim 1, wherein a maxilla bone extension apparatus is made exclusively for each patient made with a method of taking a mould of maxilla dentition arch of each patient in advance to an oral surgery, a metal sash band is wound around the peripheral of the molar teeth mould, a movable rail is welded or fixed with wax to external sides of the band.

* * * * *